United States Patent
Devellian et al.

(10) Patent No.: US 9,216,014 B2
(45) Date of Patent: Dec. 22, 2015

(54) DEVICE WITH BIOLOGICAL TISSUE SCAFFOLD FOR PERCUTANEOUS CLOSURE OF AN INTRACARDIAC DEFECT AND METHODS THEREOF

(71) Applicant: W.L. Gore & Associates, Inc., Flagstaff, AZ (US)

(72) Inventors: Carol A. Devellian, Topsfield, MA (US); Robert M. Carr, Paradise Valley, AZ (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 291 days.

(21) Appl. No.: 13/893,270

(22) Filed: May 13, 2013

(65) Prior Publication Data

US 2013/0253538 A1 Sep. 26, 2013

Related U.S. Application Data

(60) Division of application No. 11/705,380, filed on Feb. 12, 2007, now abandoned, which is a continuation of application No. 10/453,709, filed on Jun. 3, 2003, now abandoned.

(60) Provisional application No. 60/385,274, filed on Jun. 3, 2002.

(51) Int. Cl.
*A61B 1/32* (2006.01)
*A61B 17/00* (2006.01)
*A61B 17/12* (2006.01)

(52) U.S. Cl.
CPC ....... *A61B 17/0057* (2013.01); *A61B 17/12122* (2013.01); *A61B 17/12172* (2013.01);
(Continued)

(58) Field of Classification Search
CPC ................ A61B 17/0057; A61B 2017/00575; A61B 2017/00641; A61B 2017/00579; A61B 2017/00588; A61B 2017/00584; A61B 2017/00592; A61B 2017/00597; A61B 2017/00601; A61B 2017/00606
See application file for complete search history.

(56) References Cited

U.S. PATENT DOCUMENTS 2,127,903 A 8/1938 Bowen
3,562,820 A 2/1971 Braun
(Continued)

FOREIGN PATENT DOCUMENTS

EP 1013227 12/1999
EP 1046375 10/2000
(Continued)

OTHER PUBLICATIONS

Ruiz et al. "The Puncture Technique: A New Method for Transcatheter Closure of Patent Foramen Ovale." Catheterization and Cardiovascular Interventions 53, Wiley-Liss, Inc., 2001, pp. 369-372.

(Continued)

*Primary Examiner* — Mary Hoffman
(74) *Attorney, Agent, or Firm* — DLA Piper LLP (US)

(57) ABSTRACT

The invention provides an intracardiac occluder, which has biological tissue scaffolds as occlusion shells, for the percutaneous transluminal treatment of an intracardiac defect. The intracardiac occluder includes a proximal support structure supporting the proximal occlusion shell and a distal support structure supporting the distal occlusion shell. In one embodiment, biological tissue derived from the tunica submucosa layer of the porcine small intestine forms the occlusion shells.

13 Claims, 8 Drawing Sheets

(52) U.S. Cl.
  CPC .............. A61B2017/00575 (2013.01); A61B
         2017/00592 (2013.01); A61B 2017/00606
      (2013.01); A61B 2017/1205 (2013.01); A61F
                            2310/00365 (2013.01)

(56) References Cited

U.S. PATENT DOCUMENTS

| | | |
|---|---|---|
| 3,874,388 A | 4/1975 | King et al. |
| 3,875,648 A | 4/1975 | Bone |
| 3,924,631 A | 12/1975 | Mancusi |
| 4,006,747 A | 2/1977 | Kronenthal et al. |
| 4,007,743 A | 2/1977 | Blake |
| 4,425,908 A | 1/1984 | Simon |
| 4,696,300 A | 9/1987 | Anderson |
| 4,710,192 A | 12/1987 | Liotta et al. |
| 4,836,204 A | 6/1989 | Landymore et al. |
| 4,902,508 A | 2/1990 | Badylak et al. |
| 4,915,107 A | 4/1990 | Rebuffat et al. |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,108,420 A | 4/1992 | Marks |
| 5,171,259 A | 12/1992 | Inoue |
| 5,192,301 A | 3/1993 | Kamiya et al. |
| 5,222,974 A | 6/1993 | Kensey et al. |
| 5,236,440 A | 8/1993 | Hlavacek |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,334,217 A | 8/1994 | Das |
| 5,354,308 A | 10/1994 | Simon et al. |
| 5,411,481 A | 5/1995 | Allen et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,460,962 A | 10/1995 | Kemp |
| 5,478,353 A | 12/1995 | Yoon |
| 5,480,424 A | 1/1996 | Cox |
| 5,486,193 A | 1/1996 | Bourne et al. |
| 5,507,811 A | 4/1996 | Koike et al. |
| 5,540,712 A | 7/1996 | Kleshinski et al. |
| 5,573,784 A | 11/1996 | Badylak et al. |
| 5,601,571 A | 2/1997 | Moss |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,683,411 A | 11/1997 | Kavteladze et al. |
| 5,693,085 A | 12/1997 | Buirge et al. |
| 5,702,421 A | 12/1997 | Schneidt |
| 5,709,707 A | 1/1998 | Lock et al. |
| 5,711,969 A | 1/1998 | Patel et al. |
| 5,720,754 A | 2/1998 | Middleman et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,297 A | 4/1998 | Simon |
| 5,776,162 A | 7/1998 | Kleshinski |
| 5,800,516 A | 9/1998 | Fine et al. |
| 5,810,884 A | 9/1998 | Kim |
| 5,853,422 A | 12/1998 | Huebsch et al. |
| 5,855,614 A | 1/1999 | Stevens et al. |
| 5,861,003 A | 1/1999 | Latson et al. |
| 5,879,366 A | 3/1999 | Shaw et al. |
| 5,885,619 A | 3/1999 | Patel et al. |
| 5,893,856 A | 4/1999 | Jacob et al. |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,738 A | 8/1999 | Amplatz et al. |
| 5,955,110 A | 9/1999 | Patel et al. |
| 5,976,174 A | 11/1999 | Ruiz |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,024,756 A | 2/2000 | Huebsch et al. |
| 6,056,760 A | 5/2000 | Koike et al. |
| 6,077,291 A | 6/2000 | Das |
| 6,079,414 A | 6/2000 | Roth |
| 6,080,182 A | 6/2000 | Shaw et al. |
| 6,096,347 A | 8/2000 | Geddes et al. |
| 6,113,609 A | 9/2000 | Adams |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,174,322 B1 | 1/2001 | Schneidt |
| 6,187,039 B1 | 2/2001 | Hiles et al. |
| 6,190,353 B1 | 2/2001 | Makower et al. |
| 6,206,895 B1 | 3/2001 | Levinson |
| 6,206,907 B1 | 3/2001 | Marino et al. |
| 6,206,931 B1 | 3/2001 | Cook et al. |
| 6,214,029 B1 | 4/2001 | Thill et al. |
| 6,217,590 B1 | 4/2001 | Levinson |
| 6,221,092 B1 | 4/2001 | Koike et al. |
| 6,228,097 B1 | 5/2001 | Levinson et al. |
| 6,245,080 B1 | 6/2001 | Levinson |
| 6,270,515 B1 | 8/2001 | Linden et al. |
| 6,277,138 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,312,446 B1 | 11/2001 | Huebsch et al. |
| 6,315,791 B1 | 11/2001 | Gingras et al. |
| 6,319,263 B1 | 11/2001 | Levinson |
| 6,322,548 B1 | 11/2001 | Payne et al. |
| 6,334,872 B1 | 1/2002 | Termin et al. |
| 6,342,064 B1 | 1/2002 | Koike et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |
| 6,364,853 B1 | 4/2002 | French et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,440,152 B1 | 8/2002 | Gainor et al. |
| 6,443,972 B1 * | 9/2002 | Bosma et al. ................ 606/200 |
| 6,460,749 B1 | 10/2002 | Levinson et al. |
| 6,482,224 B1 | 11/2002 | Michler et al. |
| 6,488,706 B1 | 12/2002 | Solymar |
| 6,494,888 B1 | 12/2002 | Laufer et al. |
| 6,551,344 B2 | 4/2003 | Thill |
| 6,596,013 B2 | 7/2003 | Yang et al. |
| 6,623,508 B2 | 9/2003 | Shaw et al. |
| 6,623,518 B2 | 9/2003 | Thompson et al. |
| 6,712,836 B1 | 3/2004 | Berg et al. |
| 6,726,696 B1 | 4/2004 | Houser et al. |
| 8,915,958 B2 * | 12/2014 | Braido ................ 623/2.11 |
| 9,005,242 B2 * | 4/2015 | Cahill ................ 606/215 |
| 9,017,377 B2 * | 4/2015 | Steiner et al. ................ 606/213 |
| 2001/0034537 A1 | 10/2001 | Shaw et al. |
| 2001/0037129 A1 | 11/2001 | Thill |

(56) References Cited

U.S. PATENT DOCUMENTS

| | | |
|---|---|---|
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0026208 A1 | 2/2002 | Roe et al. |
| 2002/0029048 A1 | 3/2002 | Miller |
| 2002/0032462 A1 | 3/2002 | Houser et al. |
| 2002/0043307 A1 | 4/2002 | Ishida et al. |
| 2002/0052572 A1 | 5/2002 | Franco et al. |
| 2002/0077555 A1 | 6/2002 | Schwartz |
| 2002/0096183 A1 | 7/2002 | Stevens et al. |
| 2002/0099389 A1 | 7/2002 | Michler et al. |
| 2002/0107531 A1 | 8/2002 | Schreck et al. |
| 2002/0111647 A1 | 8/2002 | Khairkhahan et al. |
| 2002/0120323 A1 | 8/2002 | Thompson et al. |
| 2002/0129819 A1 | 9/2002 | Feldman et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0139819 A1 | 7/2003 | DeBeer et al. |
| 2003/0191495 A1 | 10/2003 | Ryan et al. |
| 2003/0195530 A1 | 10/2003 | Thill |
| 2004/0143291 A1 | 7/2004 | Corcoran et al. |
| 2004/0210301 A1 | 10/2004 | Obermiller |
| 2005/0043759 A1* | 2/2005 | Chanduszko ............ 606/213 |

FOREIGN PATENT DOCUMENTS

| | | |
|---|---|---|
| EP | 1222897 | 7/2002 |
| WO | WO-95/22301 | 8/1995 |
| WO | WO 96/25179 | 8/1996 |
| WO | WO 96/31157 | 10/1996 |
| WO | WO 97/28744 | 8/1997 |
| WO | WO/9807375 | 2/1998 |
| WO | WO/9918862 | 4/1999 |
| WO | WO/9918864 | 4/1999 |
| WO | WO/9918870 | 4/1999 |
| WO | WO/9918871 | 4/1999 |
| WO | WO00/27292 | 5/2000 |
| WO | WO01/08600 | 2/2001 |
| WO | WO01/49185 | 7/2001 |
| WO | WO/0178596 | 10/2001 |
| WO | WO01/93783 | 12/2001 |
| WO | WO03/061481 | 7/2003 |
| WO | WO03/073944 | 9/2003 |

OTHER PUBLICATIONS

International Search Report, International Application No. PCT/US03/17390, mailed on Oct. 6, 2003, 4 pgs.

SMST-2000, "Proceedings of the International Conference on Shape Memory and Superelastic Technologies," Apr. 30 to May 4, 2000, Asilomar Conference Center.

National Aeronautics and Space Administration, "55-Nitinol—The Alloy With a Memory: Its Physical Metallurgy, Properties, and Applications," NASA-SP 5110, pp. 24-25.

Kimura, et al., "Effects of Neutron Irradiation on the Transformation Behavior in Ti—Ni Alloys," Proceedings of the International Conference on Martensitic Transformations, 1992, pp. 935-940.

Ramanathan, et al., "Experimental and Computational Methods for Shape Memory Alloys," 15$^{th}$ ASCE Engineering Mechanics Conference, Jun. 2-5, 2002.

Shabalovskaya, "Surface, Corrosion and Biocompatibility Aspects of Nitinol as an Implant Material," Bio-Medical Materials and Engineering 12, 2002, pp. 69-109.

Uchil, "Shape Memory Alloys—Characterization Techniques," PRAMANA—Journal of Physics, vol. 58, Nos. 5 & 6, May & Jun. 2002, pp. 1131-1139.

Abraham et al. "Evaluation of the Porcine Intestinal Collagen Layer as Biomaterial" Journal of Biomed. Mater. Res., 51: 442-452 (2000).

Bailey, "The Fate of Collagen Implants in Tissue Defects," Wound Rep. Reg., 8:5-12 (2000).

Billiar et al., "Effects of Carbodiimide Crosslinking Conditions on the Physical Properties of Laminated Intestinal Submucosa," J. Biomed. Mater. Res., 56:101-108 (2001).

Edelman "Laparoscopic Herniorrhaphy with Porcine Small Intestinal Submucosa: A Preliminary Study" JSLS, 6: 203-205 (2002).

Golomb et al., "The Role of Glutaraldehydo-Induced Cross-Links in Calcification of Bovine Pericardium Used in Cardiac Valve Bioprostheses," Am. J. Pathol., 127:122-130 (1987).

Jorge-Herrero et al., "Calcification of Soft Study of Different Chemical Treatments," Tissue Employed in the Construction of Heart Valve Prostheses: Biomaterials, 12:249-252 (1991).

Huynh et al. "Remodeling of an Acellular Collagen Graft into a Physiologically Responsive Neovessel," Nature Biotechnology, 17:1083-1086 (1999).

Jux, Christian et al. "Interventional Atrial Septal Defect Closure Using a Totally Bioresorbable Occluder Matrix" Journal of the American College of Cardiology, vol. 48, No. 1, 2006: 161169.

Jux, Christian et al. "A New Biological Matrix for Septal Occlusion" Jounal of Interventional Cadiology, vol. 16, No. 2, 2003:149-152.

Mullen et al., "A Prospective, Multicenter, Phase I Clinical Trial to Evaluate the Feasibility, Efficacy, and Safety of the BioSTAR Bioabsorbable Septal Repair Implant for the Closure of Atrial-Level Shunts," Circulation, 114:1962-1967 (2006).

Ramshaw et al. "Collagen-based Biomaterials" Biotechnology and Genetic Engineering Reviews, 13:335-382 (1995).

Supplemental Partial European Search Report for EP 03 75 6366 dated Jul. 23, 2008, 3 pages.

"Intestinal Collagen" Presented in Pediatric Interventional Cardiac Symposium—PICS 2007, Structural Heart Disease Symposium. Jul. 22-25, 2007, Las Vegas, Nevada. (1 page).

Schoen et al. "Long-term failure rate and morphologic correlations in porcine bioprosthetic heart valves" Am J Cardiol. Mar. 15, 1983;51(6):957-64.

* cited by examiner

DEVICE WITH BIOLOGICAL TISSUE SCAFFOLD FOR PERCUTANEOUS CLOSURE OF AN INTRACARDIAC DEFECT AND METHODS THEREOF

CROSS-REFERENCE TO RELATED APPLICATIONS

This application is a divisional application of U.S. application Ser. No. 11/705,380 filed Feb. 12, 2007, now pending; which is a continuation application of U.S. application Ser. No. 10/453,709 filed Jun. 3, 2003, now abandoned; which claims the benefit under 35 USC §119(e) to U.S. Application Ser. No. 60/385,274 filed Jun. 3, 2002. The disclosure of each of the prior applications is considered part of and is incorporated by reference in the disclosure of this application.

BACKGROUND OF THE INVENTION

1. Field of the Invention

The invention generally relates to devices and related methods for treating intracardiac defects. More particularly, the invention provides an intracardiac occluder with a biological tissue scaffold, and related methods, for the percutaneous closure of intracardiac defects.

2. Background Information

The human heart is divided into four compartments or chambers. The left and right atria are located in the upper portion of the heart and the left and right ventricles are located in the lower portion of the heart. The left and right atria are separated from each other by a muscular wall, the intraatrial septum, while the ventricles are separated by the intraventricular septum.

Either congenitally or by acquisition, abnormal openings, holes, or shunts can occur between the chambers of the heart or the great vessels, causing blood to flow therethrough. Such deformities are usually congenital and originate during fetal life when the heart forms from a folded tube into a four chambered, two unit system. The deformities result from the incomplete formation of the septum, or muscular wall, between the chambers of the heart and can cause significant problems. Ultimately, the deformities add strain on the heart, which may result in heart failure if they are not corrected.

One such deformity or defect, a patent foramen ovale, is a persistent, one-way, usually flap-like opening in the wall between the right atrium and left atrium of the heart. Since left atrial pressure is normally higher than right atrial pressure, the flap typically stays closed. Under certain conditions, however, right atrial pressure exceeds left atrial pressure, creating the possibility for right to left shunting that can allow blood clots to enter the systemic circulation. This is particularly worrisome to patients who are prone to forming venous thrombus, such as those with deep vein thrombosis or clotting abnormalities.

Nonsurgical (i.e., percutaneous) closure of patent foramen ovales, as well as similar intracardiac defects such as atrial septal defects, ventricular septal defects, and left atrial appendages, is possible using a variety of mechanical closure devices. These devices, which allow patients to avoid the potential side effects often associated with standard anticoagulation therapies, typically consist of a metallic structural framework that is combined with a synthetic scaffold material. The synthetic scaffold material encourages ingrowth and encapsulation of the device. Current devices typically utilize a polyester fabric, expanded polytetrafluoroethylene (ePTFE), Ivalon®, or a metal mesh as the synthetic scaffold material. Such devices suffer, however, from several disadvantages, including thrombus formation, chronic inflammation, and residual leaks.

SUMMARY OF THE INVENTION

The present invention provides a device for occluding intracardiac defects. The device includes a biological tissue scaffold, as opposed to a synthetic scaffold (e.g., a polyester fabric, ePTFE, Ivalon®, or a metal mesh) as presently used by devices known in the art. In a preferred embodiment, the biological tissue scaffold is fabricated from collagen. In one embodiment, a specific type of biological tissue, derived from the tunica submucosa layer of the porcine small intestine, forms the tissue scaffold. As a result of this structure, the aforementioned disadvantages associated with the devices known in the art are minimized or eliminated.

In one aspect, the invention provides an intracardiac occluder for percutaneous transluminal treatment of an intracardiac defect. The intracardiac occluder includes a proximal support structure supporting a proximal occlusion shell and a distal support structure supporting a distal occlusion shell. The distal support structure is coupled to the proximal support structure and at least one of the occlusion shells includes a biological tissue scaffold.

Various embodiments of this aspect of the invention include the following features. The biological tissue scaffold may be a purified bioengineered type 1 collagen that may be derived from a tunica submucosa layer of a porcine small intestine. Further, in one embodiment, at least one of the support structures includes a corrosion resistant metal. Alternatively, at least one of the support structures includes a bioresorbable polymer or a biodegradable polymer. In yet another embodiment, the proximal support structure includes a plurality of outwardly extending proximal arms and the distal support structure includes a plurality of outwardly extending distal arms.

In another aspect, the invention provides a method for percutaneous transluminal treatment of an intracardiac defect in a patient. The method includes providing an intracardiac occluder as described above, positioning the intracardiac occluder proximate the intracardiac defect, and engaging the intracardiac defect with the intracardiac occluder to substantially occlude the intracardiac defect.

In one embodiment of this aspect of the invention, the intracardiac defect is engaged by positioning the proximal occlusion shell and the distal occlusion shell on different sides of the intracardiac defect. The intracardiac defect may be, for example, a patent foramen ovale, an atrial septal defect, a ventricular septal defect, or a left atrial appendage.

In yet another aspect, the invention provides a method for making an intracardiac occluder for the percutaneous transluminal treatment of an intracardiac defect. The method includes providing an overall support structure and first and second biological tissue scaffolds. The overall support structure includes a proximal support structure and a distal support structure. The method further includes coupling the first biological tissue scaffold to the proximal support structure and coupling the second biological tissue scaffold to the distal support structure. In various embodiments of this aspect of the invention, the biological tissue scaffolds are sewn, laminated, or glued to the support structures.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF THE INVENTION

The present invention provides an intracardiac occluder for the repair of intracardiac defects, such as, for example, a patent foramen ovale, an atrial septal defect, a ventricular septal defect, and left atrial appendages. The intracardiac occluder includes a structural framework and a biological tissue scaffold adhered thereto.

Figure 1:
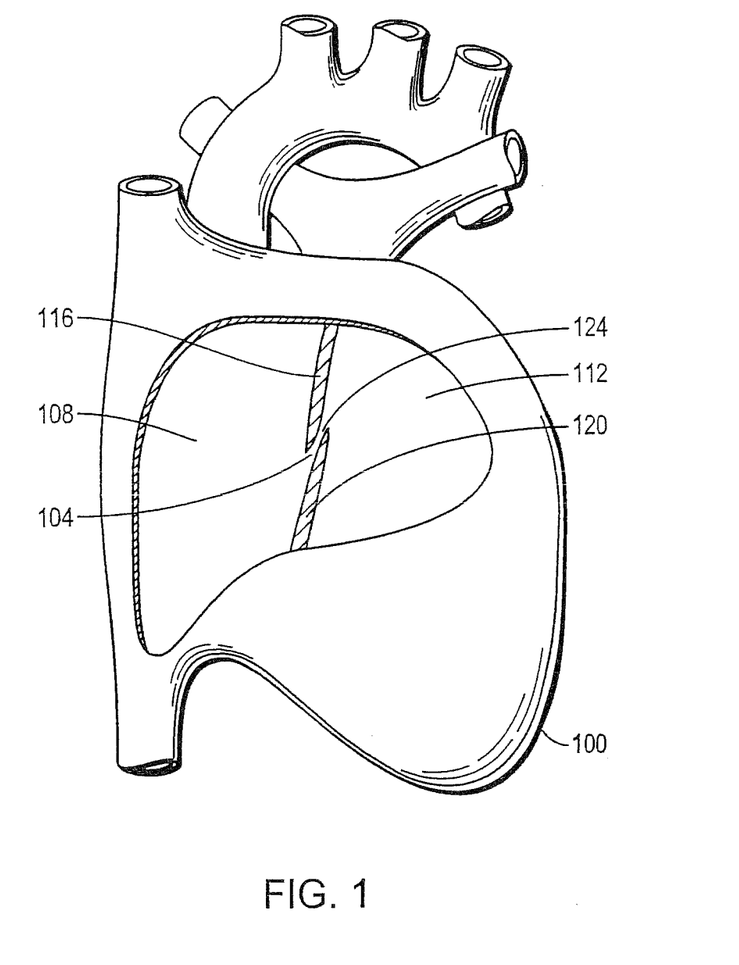
FIG. 1 is a cutaway view of a heart illustrating an intracardiac defect.

FIG. 1 depicts a cutaway view of a heart 100. The heart 100 includes a septum 104 that divides a right atrium 108 from a left atrium 112. The septum 104 includes a septum primum 116, a septum secundum 120, and an exemplary intracardiac defect 124, which is to be corrected by the intracardiac occluder of the present invention, between the septum primum 116 and the septum secundum 120. Specifically, a patent foramen ovale 124 is shown as an opening through the septum 104. The patent foramen ovale 124 provides an undesirable fluid communication between the right atrium 108 and the left atrium 112. Under certain conditions, a large patent foramen ovale 124 in the septum 104 would allow for the shunting of blood from the right atrium 108 to the left atrium 112. If the patent foramen ovale 124 is not closed or obstructed in some manner, a patient is placed at high risk for an embolic stroke.

Figure 2A:
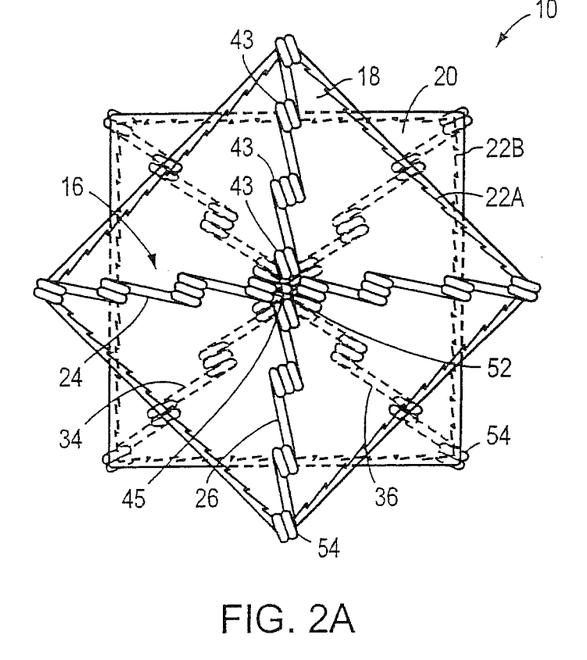
FIG. 2A is a top plan view of an intracardiac occluder according to an illustrative embodiment of the invention.
Figure 2B:
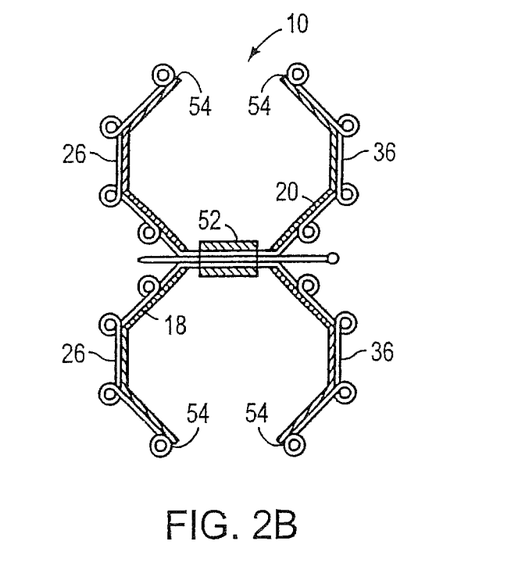
FIG. 2B is a cross-sectional view of the illustrative intracardiac occluder of FIG. 2A.

FIG. 2A depicts an intracardiac occluder 10 according to an illustrative embodiment of the invention. As shown, the intracardiac occluder 10 includes a proximal occlusion shell 18 (i.e., an occlusion shell that is closest to an operator of the intracardiac occluder 10 (e.g., a physician)), an opposite distal occlusion shell 20, and an overall support structure 16. The overall support structure 16 includes a proximal support structure 24, for supporting the proximal occlusion shell 18, and a distal support structure 34, for supporting the distal occlusion shell 20. In one embodiment, both the proximal support structure 24 and the distal support structure 34 include outwardly extending arms to support each of their respective occlusion shells 18, 20. As shown in FIG. 2A, for example, the proximal support structure 24 includes four outwardly extending arms 26 and the distal support structure 34 similarly includes four outwardly extending arms 36. In one embodiment, each outwardly extending arm is resiliently biased as a result of including three or more resilient coils 43 radially spaced from a center point 45. Alternatively, other resilient support structures could be used. In one embodiment, the eight arms 26, 36 are mechanically secured together by wire 52. Alternatively, other means, such as, for example, laser welding, may be used to secure the eight arms 26, 36 together. A cross-sectional view of the intracardiac occluder 10 illustrated in FIG. 2A, showing four arms 26, 36, is depicted in FIG. 2B.

Figure 3A:
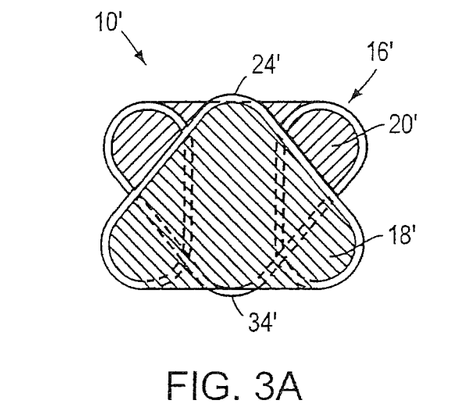
FIG. 3A is a top plan view of an intracardiac occluder according to another illustrative embodiment of the invention.
Figure 3B:
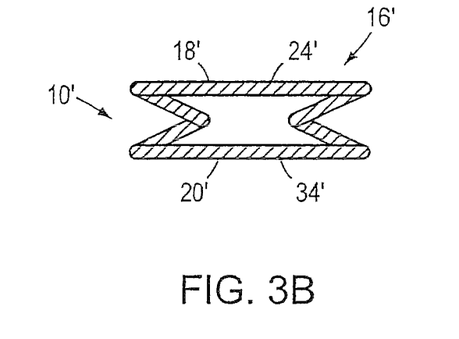
FIG. 3B is a side view of the illustrative intracardiac occluder of FIG. 3A.

FIGS. 3A and 3B depict an intracardiac occluder 10' according to another illustrative embodiment of the invention. An overall support structure 16' forms a clip and includes a proximal support structure 24', for supporting a proximal occlusion shell 18', and a distal support structure 34', for supporting a distal occlusion shell 20'.

Figure 4:
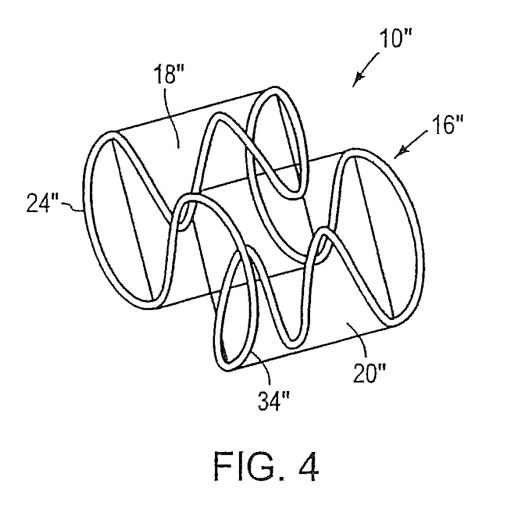
FIG. 4 is a perspective view of an intracardiac occluder according to another illustrative embodiment of the invention.

An intracardiac occluder 10" according to yet another illustrative embodiment of the invention is illustrated in FIG. 4. Again, an overall support structure 16" forms a clip and includes a proximal support structure 24", for supporting a proximal occlusion shell 18", and a distal support structure 34", for supporting a distal occlusion shell 20".

Alternatively, the overall support structure 16 may assume any shape or configuration to form the proximal support structure 24 and the distal support structure 34.

In one embodiment, the overall support structure 16 is fabricated from a corrosion resistant metal, such as, for example, stainless steel, nitinol, or a nickel-cobalt-chromium-molybdenum alloy (e.g., MP35N). Alternatively, in other embodiments, the overall support structure 16 is fabricated from bioresorbable or biodegradable polymers.

In accordance with the present invention, the occlusion shells 18, 20, which are attached, as described below, to the proximal support structure 24 and the distal support structure 34, respectively, are made from a biological tissue scaffold. In a preferred embodiment, the tissue scaffold is fabricated from collagen. In one embodiment, a purified (acellular) bioengineered type 1 collagen derived from the tunica submucosa layer of the porcine small intestine forms the tissue scaffold. More specifically, the tunica submucosa layer, referred to hereinafter as the Intestinal Collagen Layer ("ICL"), is separated or delaminated from the other layers of the porcine small intestine (i.e., the tunica muscularis and the tunica mucosa) by any method known in the art. For example, a Bitterling sausage casing machine is used to perform the separation. Once mechanically separated from the other layers, the ICL is, in one embodiment, chemically cleaned to remove debris and other substances, other than collagen. For example, the ICL is soaked in a buffer solution at 4 degrees Celsius without the use of any detergents, or, alternatively, in a second embodiment, it is soaked with NaOH or trypsin. Other cleaning techniques known to those skilled in the art may also be used. After cleaning, the ICL is decontaminated. Any sterilization system for use with collagen, as known in the art, may be used. For example, a dilute peracetic acid solution, gamma sterilization, or electron-beam sterilization is used to decontaminate the ICL.

Alternatively, collagenous tissue from the fascia lata, pericardium, or dura matter of pigs or other mammalian sources, such as, for example, cows or sheep, may form the tissue scaffold. Additionally, in making the occlusion shells 18, 20, two or more collagen layers may be bonded together and then cross-linked to produce a biocompatible material capable of being remodeled by the host cells.

In one embodiment, the biological tissue scaffold is non-porous and prevents the passage of fluids that are intended to be retained by the implantation of the intracardiac occluder 10. In another embodiment, heparin is ionically or covalently bonded to the biological tissue scaffold to render it non-thrombogenic. In yet other embodiments, proteins or cells are applied to the biological tissue scaffold to render it non-thrombogenic and/or accelerate the healing process. Growth factors may also be applied to the biological tissue scaffold to accelerate the healing process.

Referring again to FIG. 2A, the occlusion shells 18, 20 are, in one embodiment, generally square in shape. Alternatively, the occlusion shells 18, 20 may assume other shapes. The biological tissue scaffold forming the occlusion shells 18, 20 is strong and flexible. The occlusion shells 18, 20 therefore easily attach to the overall support structure 16 and, as explained below, withstand sheath delivery to an anatomical site in the body of a patient. In one embodiment, the occlusion shells 18, 20 are sewn, as at 22A, 22B, with any commonly used suture material (e.g., a polyester suture) that threads through the distal ends 54 of the respective arms 26, 36 of the proximal support structure 24 and the distal support structure 34. Alternatively, the occlusion shells 18, 20 are laminated, glued, or attached by, for example, hooks or thermal welding to the proximal support structure 24 and the distal support structure 34. In yet another embodiment, the occlusion shells 18, 20 are laminated to the overall support structure 16 and, additionally, to one another, such that the overall support structure 16 is encapsulated entirely within the occlusion shells 18, 20.

Figure 5A:
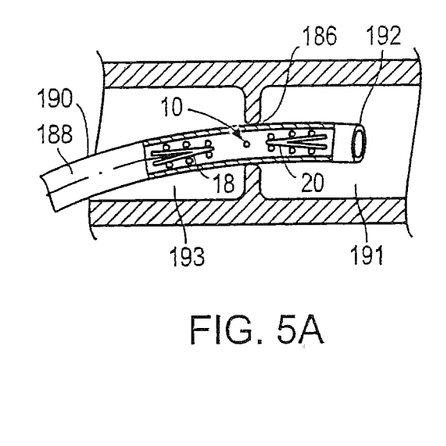
FIGS. 5A-5E illustrate the stages, according to an illustrative embodiment of the invention, for delivering an intracardiac occluder to an anatomical site in the body of a patient.
Figure 5B:
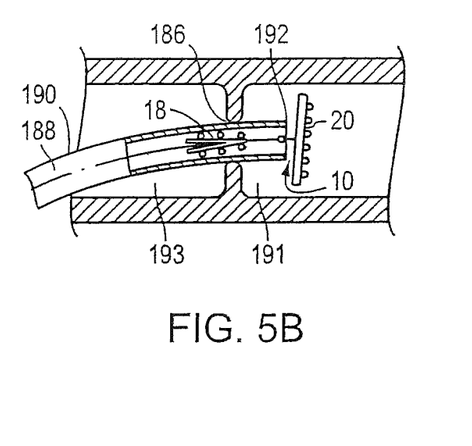
Figure 5C:
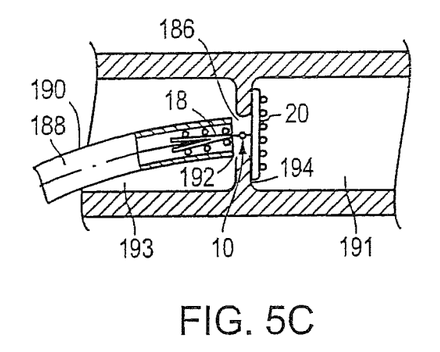
Figure 5D:
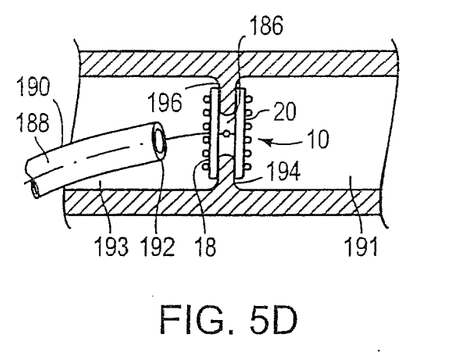
Figure 5E:
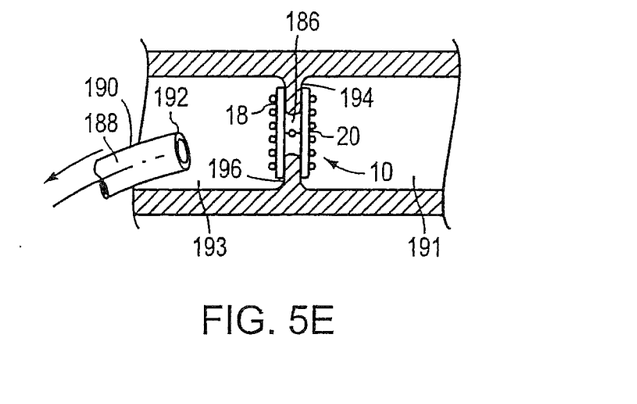

FIGS. 5A-5E depict the stages for delivering the intracardiac occluder 10, according to an illustrative embodiment of the invention, percutaneously to an anatomical site in the body of a patient. Referring to FIG. 5A, a sheath 190 is first inserted into the intracardiac defect 186 as is typically performed by one skilled in the art. The intracardiac occluder 10 is then loaded into the lumen 188 of the sheath 190 and advanced throughout the lumen 188 until positioned at the distal end 192 of the sheath 190. Referring to FIG. 5B, the distal occlusion shell 20 of the intracardiac occluder 10 is released into the distal heart chamber 191 through the distal end 192 of the sheath 190. The distal occlusion shell 20 opens automatically and resiliency. The sheath 190 is then pulled back into the proximal heart chamber 193, as illustrated in FIG. 5C, to seat the distal occlusion shell 20 against the distal wall surface 194 of the intracardiac defect 186. The intracardiac defect 186 is thereby occluded from the distal side. As shown in FIG. 5D, the sheath 190 is then further withdrawn a sufficient distance to allow the proximal occlusion shell 18 to be released from the distal end 192 of the sheath 190. The proximal occlusion shell 18 opens automatically and resiliently to lie against the proximal surface 196 of the intracardiac defect 186, occluding the intracardiac defect 186 from the proximal side. The sheath 190 is then withdrawn from the patient's body, leaving behind the opened intracardiac occluder 10. As shown in FIG. 5E, the occlusion shells 18, 20 are positioned on either side of the intracardiac defect 186 and the intracardiac occluder 10 is permanently implanted within the body of the patient.

Figure 6A:
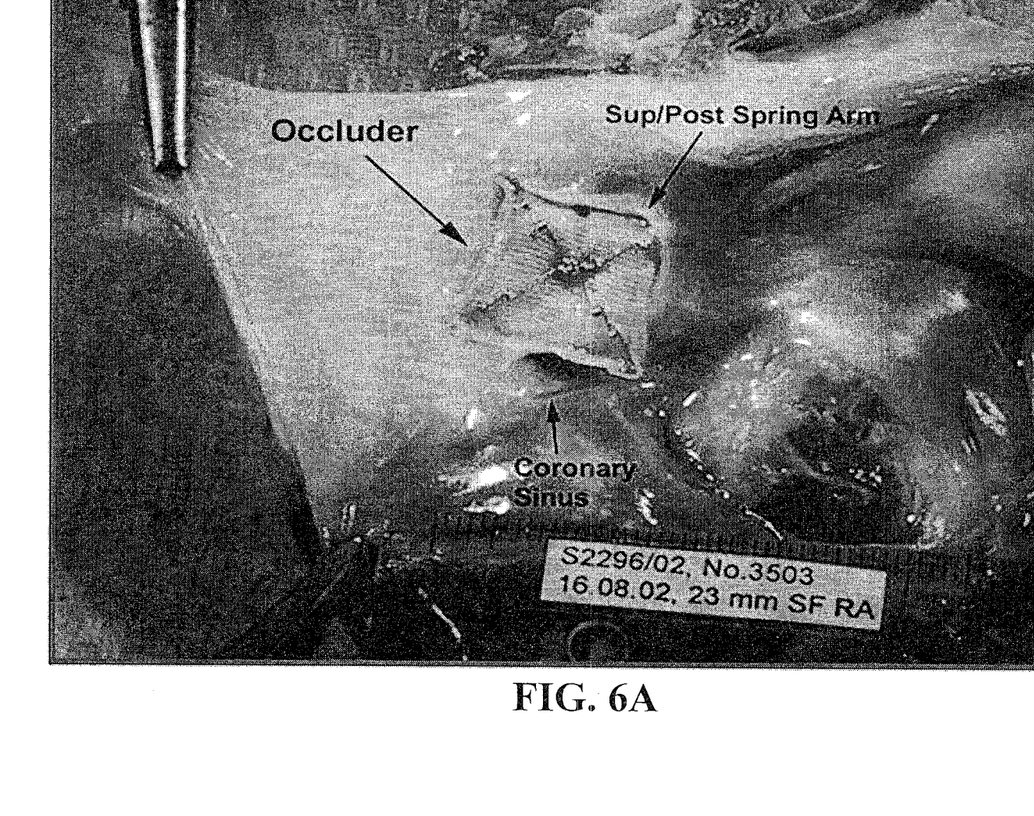
FIG. 6A illustrates the results from occluding an intracardiac defect with an intracardiac occcluder known in the art, 30-days after delivery of the intracardiac occluder.
Figure 6B:
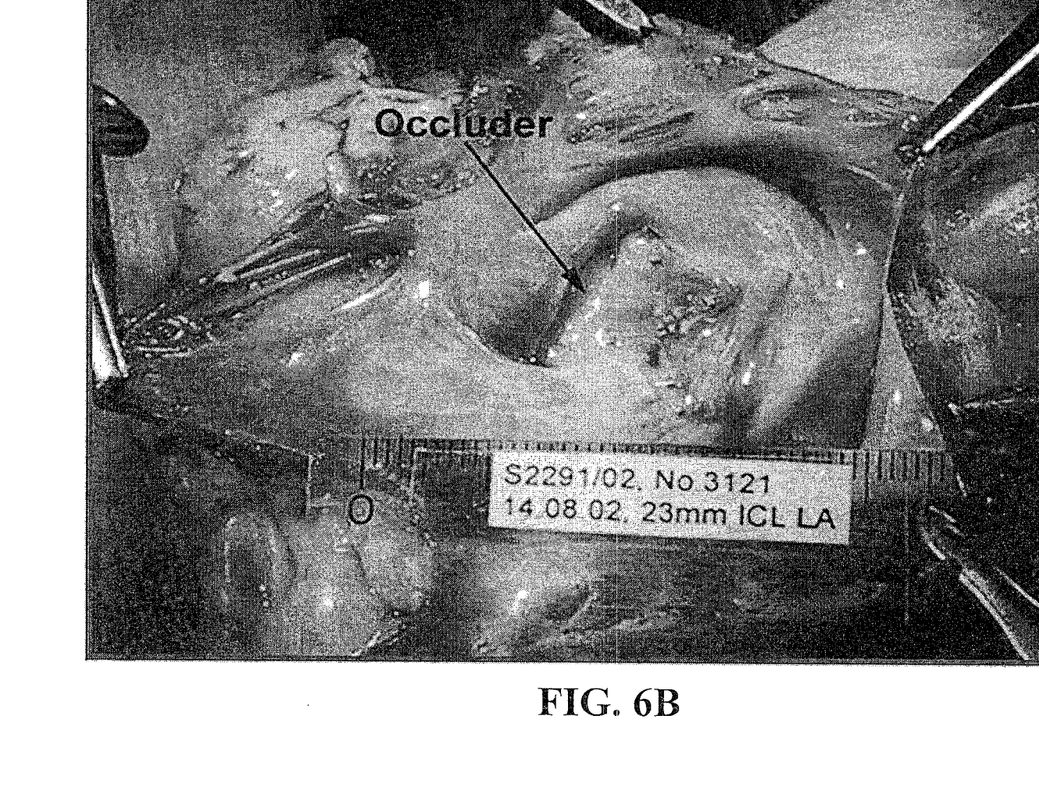
FIG. 6B illustrates the results from occluding an intracardiac defect with an intracardiac occluder according to the invention, 30-days after delivery of the intracardiac occluder.
Figure 7A:
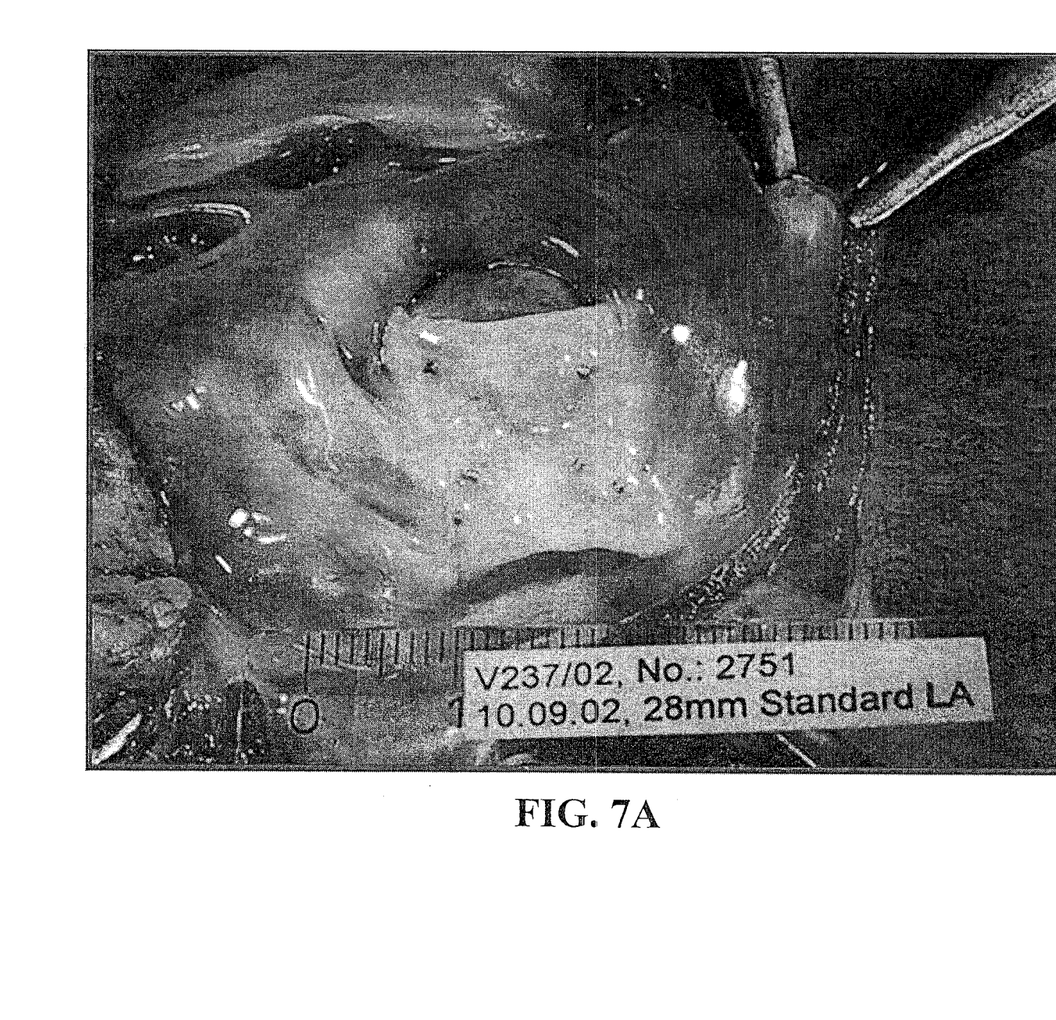
FIG. 7A illustrates the results from occluding an intracardiac defect with an intracardiac occcluder known in the art, 90-days after delivery of the intracardiac occluder.
Figure 7B:
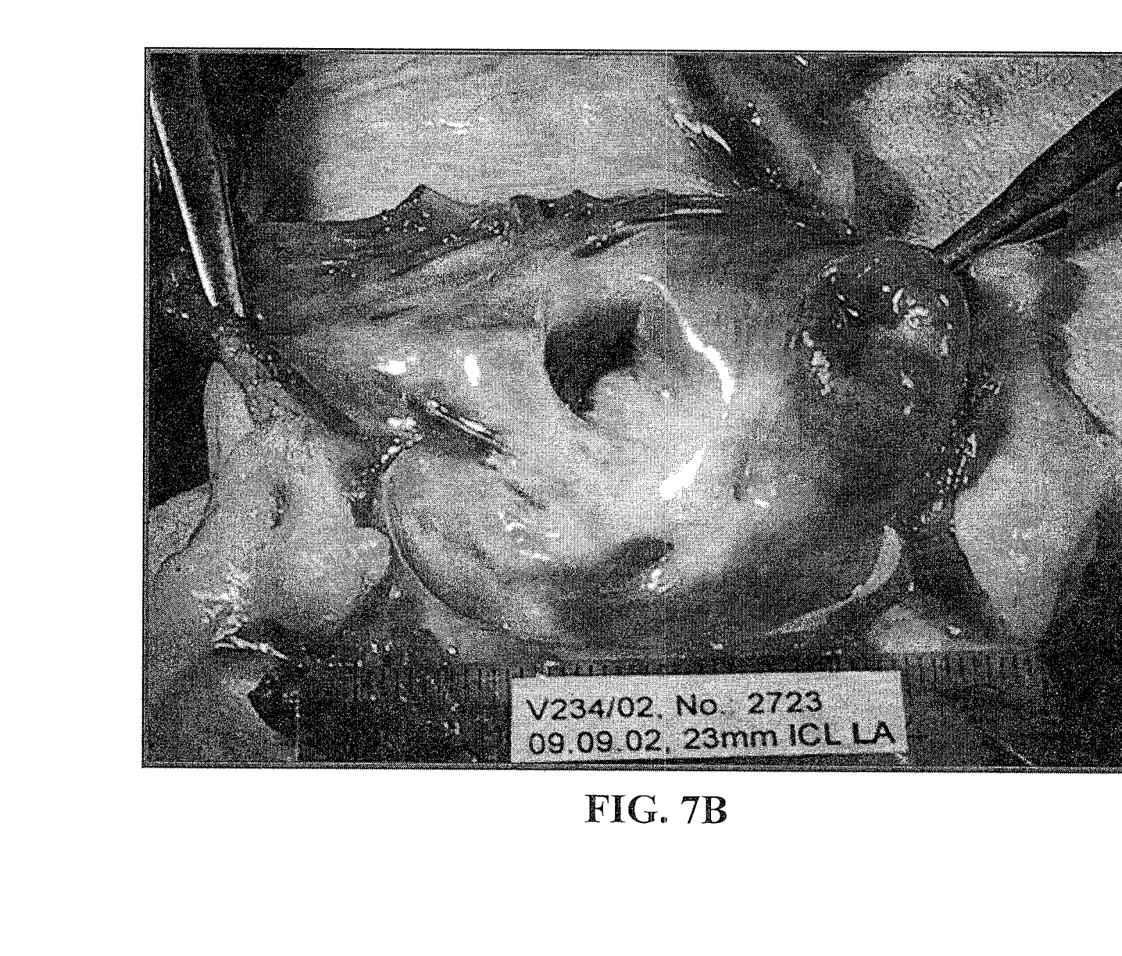
FIG. 7B illustrates the results from occluding an intracardiac defect with an intracardiac occcluder according to the invention, 90-days after delivery of the intracardiac occluder.

FIGS. 6A-6B and 7A-7B depict comparative 30-day and 90-day results, respectively, for the percutaneous closures of interventionally created intracardiac defects in sheep. Specifically, FIGS. 6A and 7A depict the 30-day and 90-day results, respectively, when an exemplary intracardiac occluder known in the art, whose occlusion shells were fabricated from a polyester fabric (i.e., a synthetic scaffold material), is used to occlude the intracardiac defect. FIGS. 6B and 7B depict the 30-day and 90-day results, respectively, when the intracardiac occluder 10 of the instant invention, whose occlusion shells 18, 20 were fabricated from ICL, is used to occlude the intracardiac defect.

As shown, the biological tissue scaffold of the intracardiac occluder 10 of the present invention increases the rate of tissue ingrowth and, consequently, decreases the time needed to completely close the intracardiac defect. Specifically, referring now to FIG. 7B, the intracardiac occluder 10 of the present invention is barely visible after 90-days. The surrounding tissue ingrowth nearly completely envelopes the intracardiac occluder 10. In comparison, referring now to FIG. 7A, the exemplary intracardiac occluder known in the art is still clearly visible after the same period of time.

As also shown, the intracardiac occluder 10 of the present invention naturally adheres to, and seals completely along, the edge of the intracardiac defect in a manner that is much improved from the exemplary intracardiac occluder known in the art. Additionally, in one embodiment, the biological tissue scaffold of the intracardiac occluder 10 of the present invention is non-porous. As a result, the intracardiac occluder 10 decreases the likelihood of fluid (e.g., blood) leakage through the opening.

Further advantages to the intracardiac occluder 10 of the present invention, in comparison to known intracardiac occluders, include decreased thrombogenicity, quicker endothelialization, superior biocompatibility, minimal foreign body reaction, decreased inmmunological and inflammatory responses, and no fibrosis.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. An intracardiac occluder clip for permanent implantation in the percutaneous transluminal space to treat an intracardiac defect so as to substantially close the intracardiac defect through host tissue endothelialization, said occluder comprising:
   a resilient wire forming opposing proximal and distal support structures for occlusion shells, wherein each support structure is formed of two external stems and two internal stems forming a M-shaped arcuate length of the wire, wherein both external stems of each M-shaped support structure are joined to the external stems of the opposing M-shaped support structure;
   a proximal occlusion shell providing a scaffold for endothelialization, wherein the shell is formed of a non-porous bioresorbable sheet and is fitted securely between the external and internal stems of the M-shaped proximal support structure; and,
   a distal occlusion shell providing a scaffold for endothelialization, wherein the shell is formed of a non-porous bioresorbable sheet and is fitted securely between the external and internal stems of the M-shaped distal support structure.

2. The occluder of claim 1, wherein the bioresorbable sheet is purified bioengineered type 1 collagen.

3. The occluder of claim 2, wherein the purified bioengineered type 1 collagen is derived from a tunica submucosa layer of the intestine.

4. The occluder of claim 1, wherein the wire is fabricated from a corrosion resistant metal.

5. The occluder of claim 1, wherein at the wire is fabricated a bioresorbable polymer.

6. The occluder of claim 1, wherein the wire is fabricated from a biodegradable polymer.

7. The occluder of claim 1, wherein the collagen sheet is treated to be non-thrombogenic.

8. A method for treating a septal defect in a heart, the method comprising:
   (a) compressing the occluder of claim 1 into the distal end of a catheter sheath;
   (b) introducing the sheath into the heart and through the septal defect to position its distal end on the distal surface of the septal defect;
   (c) extending the distal occlusion shell out of the sheath to automatically and resiliently seat the shell against the distal side of the septal defect;
   (d) withdrawing the sheath to position its distal end of the sheath at the proximal surface of the septal defect;
   (e) extending the proximal occlusion shell out of the sheath to automatically and resiliently seat the shell against the proximal side of the septal defect; and,
   (f) releasing the occluder to leave it in the septal defect and withdrawing the sheath from the heart.

9. The method of claim 8, wherein the intracardiac defect is a patent foramen ovale.

10. The method of claim 8, wherein the intracardiac defect is an atrial septal defect.

11. The method of claim 8, wherein the intracardiac defect is a ventricular septal defect.

12. The method of claim 8, wherein the intracardiac defect is a left atrial appendage.

13. The method of claim 8, further comprising step (g), confirming after at least 90 days that endotheliazaiton of the occlusion shells has occurred.

* * * * *